(12) United States Patent
Voyles et al.

(10) Patent No.: US 6,540,721 B1
(45) Date of Patent: Apr. 1, 2003

(54) BALLOON CATHETER WITH FLEXIBLE RADIOPAQUE POLYMERIC MARKER

(75) Inventors: Carolyn Voyles, Escondido, CA (US); Cheryl Rice, San Diego, CA (US); Jeong S. Lee, Diamond Bar, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/474,620

(22) Filed: Dec. 29, 1999

(51) Int. Cl.⁷ .............................................. A61M 29/00
(52) U.S. Cl. ................................................... 604/103.1
(58) Field of Search ...................... 604/96.01, 103.1, 604/103.11, 103.12, 264

(56) References Cited

U.S. PATENT DOCUMENTS

| | | | |
|---|---|---|---|
| 3,605,750 A | 9/1971 | Sheridan et al. ............. | 128/348 |
| 3,618,614 A | 11/1971 | Flynn ......................... | 128/348 |
| 4,431,238 A | 2/1984 | Evans ......................... | 312/184 |
| 4,571,240 A | 2/1986 | Samson et al. ................ | 604/96 |
| 4,581,390 A | 4/1986 | Flynn ......................... | 523/112 |
| 4,588,399 A | 5/1986 | Nebergall et al. ............ | 604/280 |
| 4,796,637 A | 1/1989 | Mascuch et al. ............. | 128/658 |
| 4,921,483 A | 5/1990 | Wijay et al. .................. | 604/96 |
| 4,938,220 A | 7/1990 | Mueller, Jr. .................. | 128/658 |
| 4,946,466 A * | 8/1990 | Pinchuk et al. .............. | 606/192 |
| 4,990,138 A | 2/1991 | Bacich et al. ................. | 604/96 |
| 5,045,071 A | 9/1991 | McCormick et al. ........ | 604/280 |
| 5,300,048 A * | 4/1994 | Drewes, Jr. et al. ......... | 604/280 |
| 5,409,006 A | 4/1995 | Buchholtz et al. ..... | 128/660.03 |
| 5,429,617 A | 7/1995 | Hammersmark et al. ... | 604/264 |
| 5,499,973 A | 3/1996 | Saab ............................ | 604/96 |
| 5,549,552 A * | 8/1996 | Peters et al. .................. | 604/96 |
| 5,554,121 A | 9/1996 | Ainsworth et al. ........... | 604/96 |
| 5,693,015 A | 12/1997 | Walker et al. ................ | 604/96 |
| 5,709,658 A | 1/1998 | Sirhan et al. ................ | 604/102 |
| 5,743,875 A | 4/1998 | Sirhan et al. ................ | 604/96 |
| 5,769,868 A | 6/1998 | Yock ........................... | 606/194 |
| 5,776,141 A * | 7/1998 | Klein et al. .................. | 606/108 |
| 5,807,355 A | 9/1998 | Ramzipoor et al. ......... | 604/282 |
| 5,827,312 A | 10/1998 | Brown et al. ................ | 606/167 |
| 5,846,199 A | 12/1998 | Hijlkema et al. ............ | 600/345 |
| 6,036,682 A | 3/2000 | Lange et al. ................. | 604/529 |
| 6,164,283 A * | 12/2000 | Lesh ........................... | 128/898 |
| 6,179,811 B1 | 1/2001 | Fugoso et al. ........... | 604/96.01 |

OTHER PUBLICATIONS

NXT PTCA Catheter Medtronic,Inc. 1998.

* cited by examiner

*Primary Examiner*—Anhtuan T. Nguyen
*Assistant Examiner*—Ann Y Lam
(74) *Attorney, Agent, or Firm*—Fulwider Patton Lee & Utecht, LLP

(57) ABSTRACT

An elongated intracorporeal device, more specifically, a balloon catheter having an elongate shaft with a distal section. The distal section of the shaft has a distal inner tubular member with an inflatable balloon disposed about the distal inner tubular member. A radiopaque marker formed at least in part of a polymer is disposed on the distal inner tubular member. The flexible radiopaque marker can be formed either by doping a desired portion of the distal inner tubular member with an appropriate radiopaque material, or preforming the radiopaque marker from a polymer doped with a radiopaque material and subsequently securing the radiopaque marker to the distal inner tubular member.

19 Claims, 2 Drawing Sheets

BALLOON CATHETER WITH FLEXIBLE RADIOPAQUE POLYMERIC MARKER

BACKGROUND

The present invention is directed to elongate intracorporeal devices, and particularly intraluminal devices for stent deployment, percutaneous transluminal coronary angioplasty (PTCA), and the similar procedures that are facilitated by an inflatable tubular member. PTCA is a widely used procedure for the treatment of coronary heart disease. In this procedure, a balloon dilatation catheter is advanced into the patient's coronary artery and the balloon on the catheter is inflated within the stenotic region of the patient's artery to open up the arterial passageway and increase the blood flow through the artery. To facilitate the advancement of the dilatation catheter into the patient's coronary artery, a guiding catheter having a preshaped distal tip is first percutaneously introduced into the cardiovascular system of a patient by the Seldinger technique through the brachial or femoral arteries. The catheter is advanced therein until the preshaped distal tip of the guiding catheter is disposed within the aorta adjacent the ostium of the desired coronary artery. A balloon dilatation catheter may then be advanced through the guiding catheter into the patient's coronary artery until the balloon on the catheter is disposed within the stenotic region of the patient's artery.

Once properly positioned across the stenosis, the balloon is inflated one or more times to a predetermined size with radiopaque liquid at relatively high pressures (e.g., generally 4–12 atmospheres) to dilate the stenosed region of a diseased artery. After the inflations, the balloon is finally deflated so that the dilatation catheter can be removed from the dilatated stenosis to resume blood flow.

Similarly, balloon catheters may be used to deploy endoprosthetic devices such as stents. Stents are generally cylindrical shaped intravascular devices that are placed within a damaged artery to hold it open. The device can be used to prevent restenosis and to maintain the patency of blood vessel immediately after intravascular treatments. Typically, a compressed or otherwise small diameter stent is disposed about an expandable member such as a balloon on the distal end of a catheter, and the catheter and stent thereon are advanced through the patient's vascular system. Inflation of the balloon expands the stent within the blood vessel. Subsequent deflation of the balloon allows the catheter to be withdrawn, leaving the expanded stent within the blood vessel.

Typically, the distal section of a balloon catheter or other percutaneous device will have a radiopaque marker in order for the operator of the device to see it under x-ray or flouroscopy imaging. Generally, a band or ring of solid radiopaque metal is secured about an inner or outer shaft of a balloon catheter to serve as a radiopaque marker. Such a configuration, however, adds stiffness and discontinuity to the catheter shaft as the solid metal bands are relatively inflexible compared to a polymer balloon catheter shaft. What has been needed is a radiopaque marker for intracorporeal devices that adds little or no longitudinal stiffness to the device.

SUMMARY

The invention is directed to a balloon catheter having an elongate shaft with a proximal section and a relatively short distal section. The distal section has a distal inner tubular member with a longitudinal axis, an outer surface and an inner surface. An inflatable balloon is disposed about the distal inner tubular member. A radiopaque marker made at least in part of a polymer has an outer surface which is substantially radially congruent with the outer surface of the distal inner tubular member from the longitudinal axis of the distal inner tubular member. An inside surface of the radiopaque marker can optionally be substantially radially congruent with the inside surface of the distal inner tubular member, or the inside surface of the radiopaque marker can be disposed between the inside surface of the distal inner tubular member and the outer surface of the radiopaque marker.

In one embodiment, the radiopaque marker can be a portion of the material of the distal inner tubular member which has been doped with a radiopaque material such as tungsten, bismuth, tantalum, barium, barium sulfate, compounds thereof or the like. In another embodiment, the radiopaque marker can be a separate discrete polymer member that is made of a radiopaque polymer or a radiolucent polymer doped with one or more radiopaque materials. The polymer of the radiopaque marker can be linear low density polyethylene, polyether block amide, alpha olefin copolymers, or the like, and can have a shore hardness or durometer selected so that the radiopaque marker and elongate inner tubular member which is axially coextensive with the radiopaque marker has a desired combined longitudinal stiffness. The combined longitudinal stiffness of the distal inner tubular member axially coextensive with the radiopaque marker and radiopaque marker can be selected such that it is substantially equal to or less than the nominal longitudinal stiffness of the distal inner tubular member axially adjacent the radiopaque marker.

Finally, two or more radiopaque markers as discussed above can be disposed along the distal inner tubular member. The radiopaque markers can be axially disposed at a proximal end of the inflatable balloon, a distal end of the inflatable balloon, at predetermined spacing to provide for a measuring function, or any other desired location or locations along the distal inner tubular member. These and other advantages of the invention will become more apparent from the following detailed description of the invention when taken in conjunction with the accompanying exemplary drawings.

DETAILED DESCRIPTION

Figure 1:
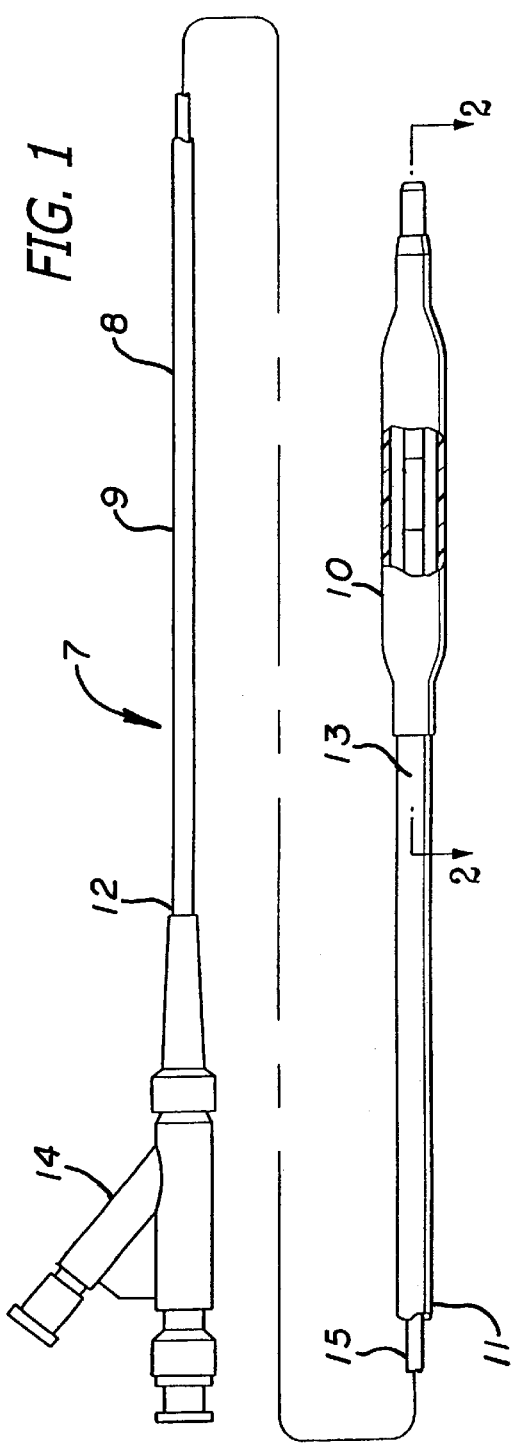
FIG. 1 shows an elevational view in partial section of a balloon catheter having features of the invention.
Figure 2:
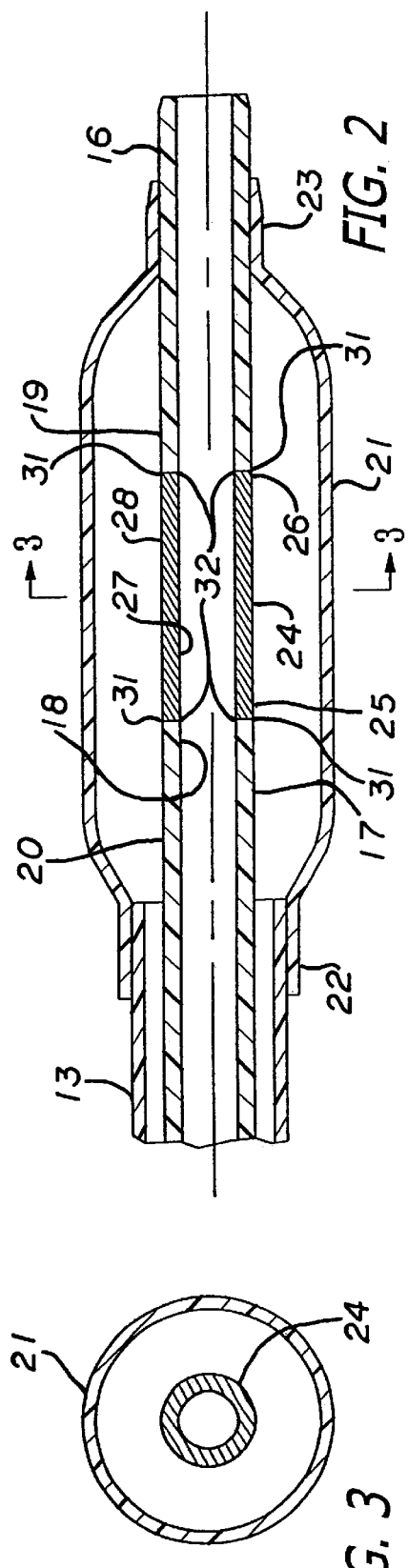
FIG. 2 is a longitudinal cross sectional view of the balloon catheter of FIG. 1 taken along lines 2—2 in FIG. 1.
Figure 3:
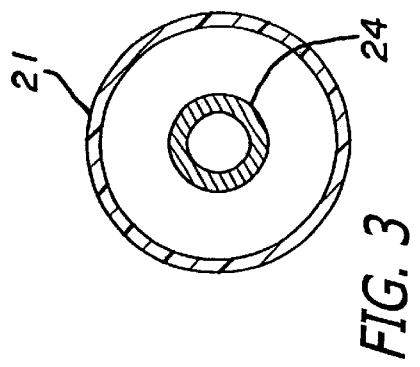
FIG. 3 is a transverse cross sectional view of the balloon catheter of FIGS. 1 and 2 taken along lines 3—3 in FIG. 2.

FIGS. 1–3 illustrate a balloon catheter 7 having features of the invention. The balloon catheter 7 has an elongate shaft with a proximal section 9 and a relatively short distal section 10. The elongate shaft 8 has an elongate outer tubular member 11 with a proximal end 12 and a distal end 13 and is secured to a proximal Y-adaptor 14 at the proximal end 12. The elongate shaft 8 also has an elongate inner tubular member 15 disposed within the elongate outer tubular member 11. The elongate inner tubular member 15 has a distal end 16 and a distal section 17. The distal section 17 of the elongate inner tubular member forms a distal inner tubular member 20 having an inner surface 18 and an outer surface 19. An inflatable balloon 21 having a proximal end 22 and a distal end 23 is disposed about the distal inner tubular member 20. The proximal end 22 of the inflatable balloon 21 is sealingly secured to the distal end 13 of the elongate outer tubular member 11. The distal end of the inflatable balloon 23 is sealingly secured to the distal end 16 of the elongate inner tubular member 15.

A radiopaque marker 24 having a proximal end 25, a distal end 26, an inner surface 27 and an outer surface 28 is disposed along the distal inner tubular member 20 between the proximal end 22 of the inflatable balloon 21 and the distal end 23 of the inflatable balloon 21. The outer surface 28 of the radiopaque marker 24 is substantially radially congruent with the outer surface 19 of the distal inner tubular member 20. In the embodiment of the balloon catheter 7 shown in FIGS. 1–3 a smooth longitudinal transition 31 between the outer surface 28 of the radiopaque marker 24 and the outer surface 19 of the distal inner tubular member 20 is formed. In addition, in the embodiment of the invention shown in FIGS. 1–3, the inside surface 27 of the radiopaque marker 24 is substantially radially congruent with the inner surface 18 of the distal inner tubular member 20. A smooth longitudinal transition 32 between the inner surface 27 of the radiopaque marker 24 and the inner surface 18 of the distal inner tubular member 20 is also shown in FIGS. 1–3.

The radiopaque marker 24 can be formed by doping a portion of the distal inner tubular member which corresponds to the dimensions of the radiopaque marker 24 with a radiopaque material such as tungsten, bismuth, tantalum, barium, barium sulfate, and compounds or alloys thereof. The radiopaque material may be in powder or particulate form which is mixed with the polymer material of the distal inner tubular member 20. Alternatively, the radiopaque marker 24 may be formed from a separate discrete member which is preformed and subsequently secured, to the distal section of the distal inner tubular member 20. Such a radiopaque marker 24 may be formed from a radiopaque polymer or a radiolucent polymer doped with a radiopaque material such as those discussed above.

In embodiments of the invention where the radiopaque marker 24 is formed from a separate discrete member, the radiopaque marker 24 may be secured to the distal inner tubular member 20 by an adhesive bond, a solvent bond, heat fusing of the radiopaque marker 24 to the distal inner tubular member 20, or by any other suitable method. In embodiments of the invention where the radiopaque marker 24 is formed from a separate discrete member formed from a radiolucent polymer doped with a radiopaque material, the radiolucent polymer can be any of a variety of suitable polymers, including, but not limited to polyethylene, linear low density polyethylene, polyether block amide, alpha olefin copolymers, polyester and polyamide.

In embodiments of the invention where the outer surface 19 of the digital inner tubular member 20 is substantially radially congruent with the outer surface 28 of the radiopaque marker 24 and the radiopaque marker 24 is made from a separate discrete member, it may be necessary to remove material from the outer surface 19 of the distal inner tubular member 20 at the site where the radiopaque marker 24 is to be secured. In this way, the radiopaque marker 24 takes the place of the removed material of the distal inner tubular member 20 and can also yield a smooth longitudinal transition 31.

In one embodiment of the invention, a thickness of material approximately equal to a wall thickness of the radiopaque marker 24 is removed from the outer surface 19 of the elongate inner tubular member 15 prior to securing the radiopaque marker 24 to the distal inner tubular member 20. In such an embodiment, the radiopaque marker 24 can be stretched circumferentially to pass over the distal end 16 of the distal inner tubular member 20 and be positioned at a site where material has been removed from the outer surface 19 of the distal inner tubular member 20. Once the circumferentially stretched radiopaque marker 24 is properly positioned axially, the radiopaque marker 24 can be relaxed to conform to the distal inner tubular member 20.

Any number of radiopaque markers 24 as described above can be secured to the distal inner tubular member 20 having the same or varied configurations. In embodiments of the invention where a plurality of radiopaque markers 24 are secured to the distal inner tubular member 20, the markers 24 may be spaced at regular intervals in order to provide a measuring tool or mechanism that can be visualized under radioscopic imaging, or the radiopaque markers 24 may be axially coextensive with and mark features of interest of the balloon catheter 7 structure, such as the proximal and distal ends 22 and 23 of the inflatable balloon 21, rapid exchange ports (not shown), a distal extremity of the catheter or the like.

The length of the elongate inner tubular member 15 and the elongate outer tubular member 11 can be up to about 300 cm, specifically, about 100 to about 200 cm. An outer diameter of the elongate outer tubular member 11 can up to about 0.2 inch, specifically about 0.01 to about 0.1 inch. In some embodiments of the invention, the elongate inner tubular member 15 has a transverse dimension or diameter sized to have an inner diameter or lumen diameter appropriate for a coronary guidewire. In such embodiments, the elongate inner tubular member 15 may have an inner diameter of about 0.012 to about 0.02 inch. However, the elongate inner tubular member 15 can have any transverse dimension that leaves a lumen between the outer surface 19 of the elongate inner tubular member 15 and an inner surface 35 of the elongate outer tubular member 11 which is suitable for injection of inflation medium into the inflatable balloon 21.

The elongate outer tubular member 11 and elongate inner tubular member 15 may be made of conventional balloon catheter shaft materials such as polyurethane, polyethylene, PEBAX, Nylon or any other suitable material. The polymer of the radiopaque marker 24 can have a shore hardness or durometer selected so that the radiopaque marker 24 and distal inner tubular member 20 which is axially coextensive with the radiopaque marker 24 has a desired combined longitudinal stiffness. The combined longitudinal stiffness of the distal inner tubular member 20 and radiopaque marker 24 can be selected such that no longitudinal stiffness is added to the elongate inner tubular member 24 at the position of the radiopaque marker 24 relative to the longitudinal stiffness of portions of the distal inner tubular member 20 adjacent the radiopaque marker 24.

The radiopaque marker 24 can have an axial length of up to about 50 mm, specifically, about 1 to about 40 mm, and more specifically, about 5 to about 30 mm, and even more specifically, about 10 to about 20 mm. The radiopaque marker 24 can have an outer transverse dimension or diameter similar to an outer transverse dimension or diameter of the distal inner tubular member 20, specifically, up to about 0.18 inch, more specifically, about 0.01 to about 0.04 inch, and more specifically, about 0.015 to about 0.025 inch. The radiopaque marker 24 may be sized and positioned so as to be axially coextensive with the inflatable balloon 21.

Figure 4:
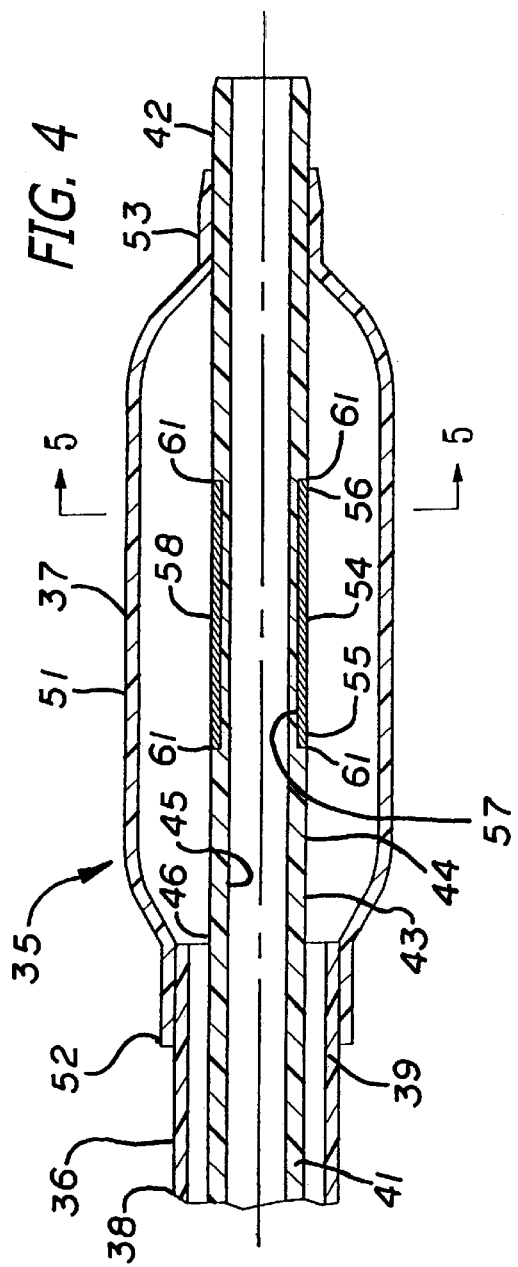
FIG. 4 is a longitudinal cross sectional view of a portion of a balloon catheter having features of the invention.
Figure 5:
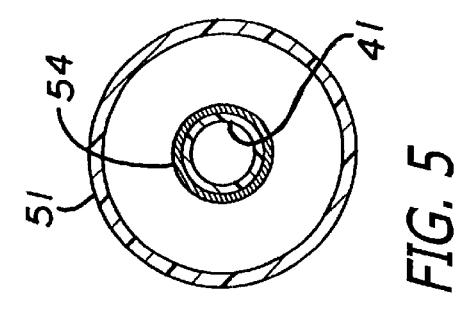
FIG. 5 is a transverse cross sectional view of the balloon catheter of FIG. 4 taken along lines 5—5 of FIG. 4.

FIGS. 4 and 5 show a portion of an embodiment of a balloon catheter 35 having features of the invention. The balloon catheter 35 has an elongate shaft 36 with a proximal section (not shown) and a relatively short distal section 37. The elongate shaft 36 has an elongate outer tubular member 38 with a distal end 39 and a proximal end secured a proximal Y-adaptor (not shown) similar to the proximal end 12 secured to the Y-adaptor 14 in FIG. 1. The elongate shaft 36 also has an elongate inner tubular member 41 is disposed within the elongate outer tubular member 38. The elongate inner tubular member 41 has a distal end 42 and a distal section 43. The distal section 43 of the elongate inner tubular member 41 forms a distal inner tubular member 44 having an inner surface 45 and an outer surface 46. An inflatable balloon 51 having a proximal end 52 and a distal end 53 has the proximal end 52 sealingly secured to the distal end 39 of the elongate outer tubular member 38. The distal end 53 of the balloon 51 is sealingly secured to the distal end 42 of the elongate inner tubular member 41.

A radiopaque marker 54 having a proximal end 55, a distal end 56, an inner surface 57 and an outer surface 58 is disposed along the distal inner tubular member 44 between the proximal end 52 of the inflatable balloon 51 and the distal end 53 of the inflatable balloon 51. The outer surface 58 of the radiopaque marker 54 is substantially radially congruent with the outer surface 46 of the distal inner tubular member 44.

In the embodiment of the balloon catheter 35 shown in FIGS. 4 and 5 a smooth longitudinal transition 61 between the outer surface 58 of the radiopaque marker 54 and the outer surface 46 of the distal inner tubular member 44 is formed. In addition, in the embodiment of the invention shown in FIGS. 4 and 5, the inner surface 57 of the radiopaque marker 54 is disposed between the inner surface 45 of the distal inner tubular member 44 and the outside surface 58 of the radiopaque marker 54.

The radiopaque marker 54 can be formed by doping a portion of the distal inner tubular member 44 which corresponds to the dimensions of the radiopaque marker 54 with a radiopaque material such as tungsten, bismuth, tantalum, barium, barium sulfate, compounds thereof or the like. The radiopaque material may be in powder or particulate form which is mixed with the polymer material of the distal inner tubular member 44. Alternatively, the radiopaque marker 54 may be formed from a separate discrete member which is preformed and subsequently secured the distal inner tubular member 44. Such a radiopaque marker 54 may be formed from a radiopaque polymer or a radiolucent polymer doped with a radiopaque material such as those discussed above. The materials, dimensions and configuration of the radiopaque marker 54, distal inner tubular member 44, elongate outer tubular member 38 and inflatable balloon 51 can be the same as the materials, dimensions and configuration of the corresponding components of the balloon catheter 10 shown in FIGS. 1–3.

Figure 6:
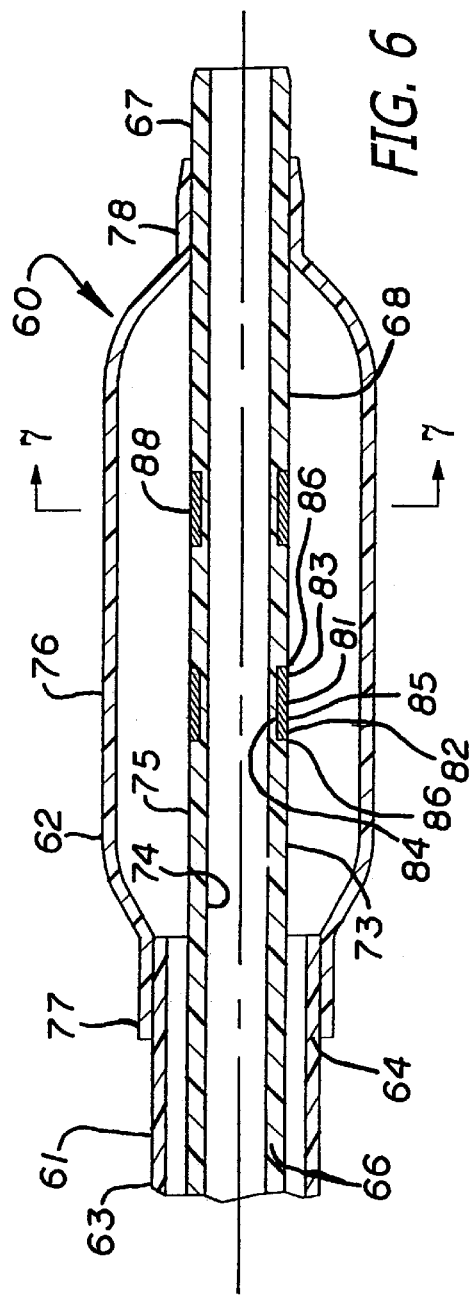
FIG. 6 is a longitudinal cross sectional view of a portion of a balloon catheter having features of the invention.
Figure 7:
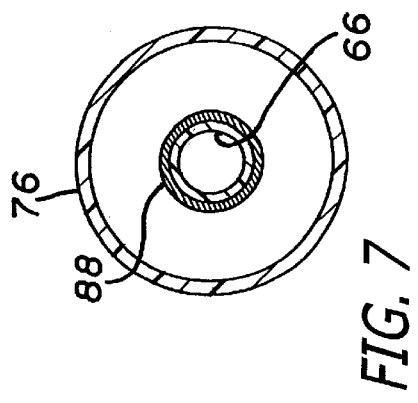
FIG. 7 is transverse cross sectional view of the balloon catheter of FIG. 6 taken along lines 7—7 in FIG. 6.

FIGS. 6 and 7 show a portion of an embodiment of a balloon catheter 60 having features of the invention. The balloon catheter 60 has an elongate shaft 61 with a proximal section (not shown) and a relatively short distal section 62.

The elongate shaft 61 has an elongate outer tubular member 63 with a distal end 64 and a proximal end secured a proximal Y-adaptor (not shown) similar to the proximal end 12 secured to the Y-adaptor 14 in FIG. 1. The elongate shaft 61 also has an elongate inner tubular member 66 is disposed within the elongate outer tubular member 63. The elongate inner tubular member 66 has a distal end 67 and a distal section 68. The distal section 68 of the elongate inner tubular member 66 forms a distal inner tubular member 73 having an inner surface 74 and an outer surface 75. An inflatable balloon 76 having a proximal end 77 and a distal end 78 has the proximal end 77 sealingly secured to the distal end 64 of the elongate outer tubular member 63. The distal end 78 of the balloon 76 is sealingly secured to the distal end 67 of the elongate inner tubular member 66.

A first radiopaque marker 81 is disposed along the distal inner tubular member 73. The first radiopaque marker 81 has a proximal end 82, a distal end 83, an inner surface 84 and an outer surface 85 is disposed along the distal inner tubular member 73 between the proximal end 77 of the inflatable balloon 76 and the distal end 78 of the inflatable balloon 76. The outer surface 85 of the first radiopaque marker 81 is substantially radially congruent with the outer surface 75 of the distal inner tubular member 73.

In the embodiment of the balloon catheter 60 shown in FIGS. 6 and 7 a smooth longitudinal transition 86 between the outer surface 85 of the first radiopaque marker 81 and the outer surface 75 of th e distal inner tubular member 73 is formed. In addition, in the embodiment of the invention shown in FIGS. 6 and 7, the inner surface 84 of the first radiopaque marker 81 is disposed between the inner surface 74 of the distal inner tubular member 73 and the outside surface 85 of the first radiopaque marker 81.

The first radiopaque marker 81 can be formed by doping a portion of the distal inner tubular member 73 which corresponds to the dimensions of the first radiopaque marker 81 with a radiopaque material such as tungsten, bismuth, tantalum, barium, barium sulfate, compounds thereof or the like. The radiopaque material may be in powder or particulate form which is mixed with the polymer material of the distal inner tubular member 73. Alternatively, the first radiopaque marker 81 may be formed from a separate discrete member which is preformed and subsequently secured the distal inner tubular member 73. Such a first radiopaque marker 81 may be formed from a radiopaque polymer or a radiolucent polymer doped with a radiopaque material such as those discussed above. The materials, dimensions and configuration of the first radiopaque marker 81, distal inner tubular member 73, elongate outer tubular member 63 and inflatable balloon 76 can be the same as the materials, dimensions and configuration of the corresponding components of the balloon catheter 10 shown in FIGS. 1–3.

A second radiopaque marker 88 disposed distally of the first radiopaque marker 81 can be formed in a manner similar to that of the first radiopaque marker 81 and can have dimensions, materials and configurations similar to those of the first radiopaque marker 81. Although FIGS. 6 and 7 show only a first and second radiopaque markers 81 and 88, any number of markers may be used and disposed along the distal inner tubular member 73 or along any other portion of the elongate inner tubular member 66 generally. In addition, the first and second radiopaque markers 81 and 88 may have distal ends spaced axially at any desired predetermined distance, such as 1, 2, 5, or 10 mm, so as to allow the operator of the balloon catheter 60 to measure features within a patient's vasculature under flouroscopy, such as lesion length and the like.

While particular forms of the invention have been illustrated and described, it will be apparent that various modifications can be made without departing from the spirit and scope of the invention. Accordingly, it is not intended that the invention be limited, except as by the appended claims.

What is claimed is:

1. A balloon catheter having an elongate shaft with a proximal section and a relatively short distal section, the distal section comprising:
    a) a distal inner tubular member comprising a first polymer, and having a longitudinal axis, an outer surface and an inner surface;
    b) an inflatable balloon disposed about the distal inner tubular member, and having a proximal end, a distal end, and an interior disposed between the proximal and distal end; and
    c) a tubular flexible radiopaque marker comprising a second polymer located at the distal inner tubular member and disposed within the inflation member interior, having an inner surface and an outer surface that is substantially radially congruent with the outer surface of the distal inner tubular member, such that the longitudinal transition between the outer surface of the marker and the outer surface of the distal inner tubular member is smooth.

2. The balloon catheter of claim 1 wherein the radiopaque marker comprises a portion of the distal inner tubular member which has been doped with a radiopaque material.

3. The balloon catheter of claim 1 wherein the radiopaque marker comprises a discrete member which is secured to the distal inner tubular member.

4. The balloon catheter of claim 3 wherein the radiopaque marker is fused by heat and pressure to the distal inner tubular member.

5. The balloon catheter of claim 3 wherein the radiopaque marker is bonded with a polymeric adhesive to the distal inner tubular member.

6. The balloon catheter of claim 1 wherein the inner surface of the radiopaque marker is disposed between the inside surface of the distal inner tubular member and the outside surface of the radiopaque marker.

7. The balloon catheter of claim 1 wherein the inner surface of the radiopaque marker is substantially radially congruent with the inside surface of the distal inner tubular member.

8. The balloon catheter of claim 1 wherein the radiopaque marker is substantially longitudinally coextensive with the inflatable balloon.

9. The balloon catheter of claim 1 wherein the radiopaque marker is about 1 to about 50 mm in length.

10. The balloon catheter of claim 1 wherein the polymer of the radiopaque marker is doped with a radiopaque material.

11. The balloon catheter of claim 10 wherein the radiopaque material is selected from the group of materials consisting of tungsten, bismuth, tantalum, barium and compound or alloy thereof.

12. The balloon catheter of claim 1 wherein the polymer of the radiopaque marker is comprised of a material selected from the group consisting of polyethylene, polyether block amide, alpha olefin copolymers, polyester and polyamide.

13. The balloon catheter of claim 1 wherein the radiopaque marker is about 1 to about 40 mm in length.

14. The balloon catheter of claim 1 wherein the radiopaque marker comprises a first radiopaque marker and further comprising a second radiopaque marker disposed on the distal inner tubular member.

15. The balloon catheter of claim 14 wherein the first radiopaque marker is disposed at a proximal end of the balloon and the second radiopaque marker is disposed at a distal end of the inflatable balloon.

16. The balloon catheter of claim 1 wherein the radiopaque marker is axially disposed between a proximal end of the inflatable balloon and a distal end of the inflatable balloon.

17. The balloon catheter of claim 1 wherein the polymer of the radiopaque marker has a shore hardness that is selected such that the combined longitudinal flexibility of the radiopaque marker and a portion of the distal inner tubular member axially coextensive with the radiopaque marker is substantially equal to, or less than the nominal longitudinal flexibility of the distal inner tubular member axially adjacent the radiopaque marker.

18. The balloon catheter of claim 1 wherein the first polymer is a different material than the second polymer.

19. The balloon catheter of claim 1 wherein the first polymer and the second polymer is the same material.

* * * * *

UNITED STATES PATENT AND TRADEMARK OFFICE
CERTIFICATE OF CORRECTION

PATENT NO.    : 6,540,721 B1
DATED         : April 1, 2003
INVENTOR(S)   : Carolyn Voyles et al.

It is certified that error appears in the above-identified patent and that said Letters Patent is hereby corrected as shown below:

<u>Title page,</u>
Item [56], U.S. PATENT DOCUMENTS, add:
-- 6,340,367     1/2002          Stinson et al. --

Signed and Sealed this

Second Day of September, 2003

JAMES E. ROGAN
*Director of the United States Patent and Trademark Office*